(12) United States Patent
Morehead

(10) Patent No.: US 7,283,615 B2
(45) Date of Patent: Oct. 16, 2007

(54) ON-DEMAND MULTIPLE STEP FLUOROSCOPE CONTROL ASSEMBLY

(76) Inventor: Brent Morehead, 530 Silver La., Rock Hill, SC (US) 29732

( * ) Notice: Subject to any disclaimer, the term of this patent is extended or adjusted under 35 U.S.C. 154(b) by 142 days.

(21) Appl. No.: 11/350,236

(22) Filed: Feb. 8, 2006

(65) Prior Publication Data

US 2007/0183574 A1    Aug. 9, 2007

(51) Int. Cl.
*H05G 1/56* (2006.01)
(52) U.S. Cl. ..................... 378/117; 378/114
(58) Field of Classification Search ............. 378/4–20, 378/38–42, 62, 63, 91, 98, 98.2–98.3, 101, 378/114–7, 145, 190, 210, 64, 65
See application file for complete search history.

(56) References Cited

U.S. PATENT DOCUMENTS

| | | | | |
|---|---|---|---|---|
| 5,091,926 A | * | 2/1992 | Horton et al. ............... | 378/114 |
| 5,127,394 A | | 7/1992 | Lane | |
| 5,206,894 A | * | 4/1993 | Makrinos et al. ............. | 378/93 |
| 5,517,021 A | * | 5/1996 | Kaufman et al. ........... | 250/221 |
| 6,368,269 B1 | * | 4/2002 | Lane .......................... | 600/126 |
| 6,486,573 B2 | * | 11/2002 | Yagi et al. .................. | 307/328 |
| 6,823,207 B1 | * | 11/2004 | Jensen et al. ................ | 600/427 |
| 7,008,074 B1 | * | 3/2006 | Halm .......................... | 362/105 |
| 7,193,773 B2 | * | 3/2007 | Haisch et al. ................ | 359/376 |
| 2002/0028997 A1 | * | 3/2002 | Ito et al. ...................... | 600/476 |

* cited by examiner

*Primary Examiner*—Allen C. Ho
*Assistant Examiner*—Anastasia S. Midkiff
(74) *Attorney, Agent, or Firm*—Schwartz Law Firm P.C.

(57) ABSTRACT

A fluoroscope includes an x-ray generator, an x-ray tube for focusing the x-rays onto an area of a patient being imaged, and a fluoroscope monitor with a display screen for viewing the image captured by the fluoroscope. An on-demand multiple step fluoroscope control assembly includes a foot control and a head control. The foot control is operatively connected to the fluoroscope and adapted for being manually actuated by a foot of an operator. The foot control defines a first step activator for controlling activation of the x-ray generator. The head control is operatively connected to the fluoroscope and adapted for being automatically actuated when the operator views the display screen. The head control defines a second step activator for controlling activation of the x-ray generator. Upon simultaneous employment of the first and second step activators, the foot control and the head control cooperate to activate the x-ray generator and output radiation to the patient. In the absence of simultaneous employment of the first and second step activators, no radiation is output to the patient.

8 Claims, 5 Drawing Sheets

ON-DEMAND MULTIPLE STEP FLUOROSCOPE CONTROL ASSEMBLY

TECHNICAL FIELD AND BACKGROUND OF THE INVENTION

This invention relates to an on-demand, multiple step fluoroscope control assembly. The invention serves to curtail needless irradiation of patients and operators during fluoroscopic exams.

During a fluoroscopic exam, a continuous, intermittent, or pulsed X-ray beam is used to view an organ or other body part in real time. The live images are displayed on a computer screen or television monitor. Fluoroscopy is most often used to view the upper and lower GI tracts, and during common medical/surgical procedures including cardiac catheterization, angiography, angioplasty, urinary/biliary stone removal, various needle-biopsies, and placement of catheters, stents, and filters.

Fluoroscopy and CT scans account today for the bulk of the doses received by patients from medical x-rays. Accumulated exposure to medical x-rays is a necessary causal co-actor in over half of the fatal cases of cancer and ischemic heart disease (IHD) in the United States. These two diseases account for over a million deaths per year in the USA.

Modern fluoroscopes have features designed to limit needless exposure radiation. Such features include the capability for last-image-hold ("freeze-frame"), which permits physicians to view and discuss an image during a procedure, without continuing to irradiate the patient. Other important features include display capability to show the operator the dose-rate per minute, the duration of exposure, and the accumulated skin-dose to the patient in "real-time" (during the procedure), and to record such doses.

Other ways to reduce x-ray exposure without compromising a procedure are more directly tied to the operator. For example, the fluoroscope is typically activated using a conventional foot switch or "fluoro pedal." In many cases, during fluoroscopic exams the operator simply forgets to remove his/her foot from the pedal while recording information in the patient file or performing other tasks incidental to the exam. In an effort to alleviate this problem, one prior art control device described in U.S. Pat. No. 5,091,926 is head-activated such that the fluoroscope is intended to function only when the operator is viewing the monitor. The device utilizes an infrared transmitter worn by the operator and an infrared receiver located on fluoroscope monitor. The object of this device is to eliminate the requirement of the foot switch in operating the fluoroscope x-ray and monitor. Replacing the foot switch, however, does not effectively prevent the inadvertent irradiation of patients. For example, the transmitter of the prior art device may be improperly positioned on the head or may become misadjusted during a procedure and accidentally directed towards the monitor.

The control device described in the '926 Patent, like the conventional fluoro pedal, provides only a single-step activation means for controlling operation of the fluoroscope. As such, operators using this device are likely to continue needlessly irradiating patients.

SUMMARY OF INVENTION

Therefore, it is an object of the invention to provide an on-demand, multiple step fluoroscope control assembly which selectively activates the fluoroscope.

It is another object of the invention to provide a fluoroscope control assembly which substantially eliminates needless and inadvertent irradiation of patients.

It is another object of the invention to provide a fluoroscope control assembly which allows the operator to study a "freeze frame" image on the display screen without needlessly irradiating the patient.

It is another object of the invention to provide a fluoroscope control assembly which incorporates both a foot control and a head control.

It is another object of the invention to provide a fluoroscope control assembly which requires simultaneous actuation of the foot and head controls in order to activate the fluoroscope.

These and other objects of the present invention are achieved in the preferred embodiments disclosed below by providing an improved fluoroscope including means for generating x-rays, an x-ray tube for focusing the x-rays onto an area of a patient being imaged, and a fluoroscope monitor with a display screen for viewing the image captured by the fluoroscope. The improvement comprises an on-demand multiple step fluoroscope control assembly. The control assembly includes a foot control operatively connected to the fluoroscope and adapted for being manually actuated by a foot of an operator. The foot control comprises a first step activation means for controlling activation of the x-ray generation means. A head control is operatively connected to the fluoroscope and adapted for being automatically actuated when the operator views the display screen. The head control comprises a second step activation means for controlling activation of the x-ray generation means. Upon simultaneous employment of the first and second step activation means, the foot control and the head control cooperate to activate the x-ray generation means and output radiation to the patient. In the absence of simultaneous employment of the first and second step activation means, no radiation is output to the patient.

According to another preferred embodiment of the invention, the head control includes an infrared transmitter.

According to another preferred embodiment of the invention, the transmitter comprises an emitter cartridge for projecting an infrared radiation beam outwardly from the operator.

According to another preferred embodiment of the invention, the emitter cartridge is attached to an ear mount adapted for being worn by the operator.

According to another preferred embodiment of the invention, the emitter cartridge is pivotably adjustable relative to the ear mount to control a projection angle of the radiation beam.

According to another preferred embodiment of the invention, an infrared receiver is operatively connected to the fluoroscope and cooperates with the transmitter to actuate the head control.

According to another preferred embodiment of the invention, the receiver defines a sensor zone which encompasses the display screen of the fluoroscope monitor, such that projection of the radiation beam onto the display screen actuates the head control.

In another embodiment, the invention is an on-demand multiple step fluoroscope control assembly adapted for use in a fluoroscope.

In yet another embodiment, the invention is a method for imaging a patient using a fluoroscope. The fluoroscope includes means for generating x-rays. The method comprises the steps of actuating a foot control operatively connected to the fluoroscope, and upon actuation of the foot control, simultaneously actuating a head control operatively connected to the fluoroscope. The foot control and head control cooperate to activate the x-ray generation means and output radiation to the patient. In the absence of simultaneous actuation of the foot control and head control, no radiation is output to the patient.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
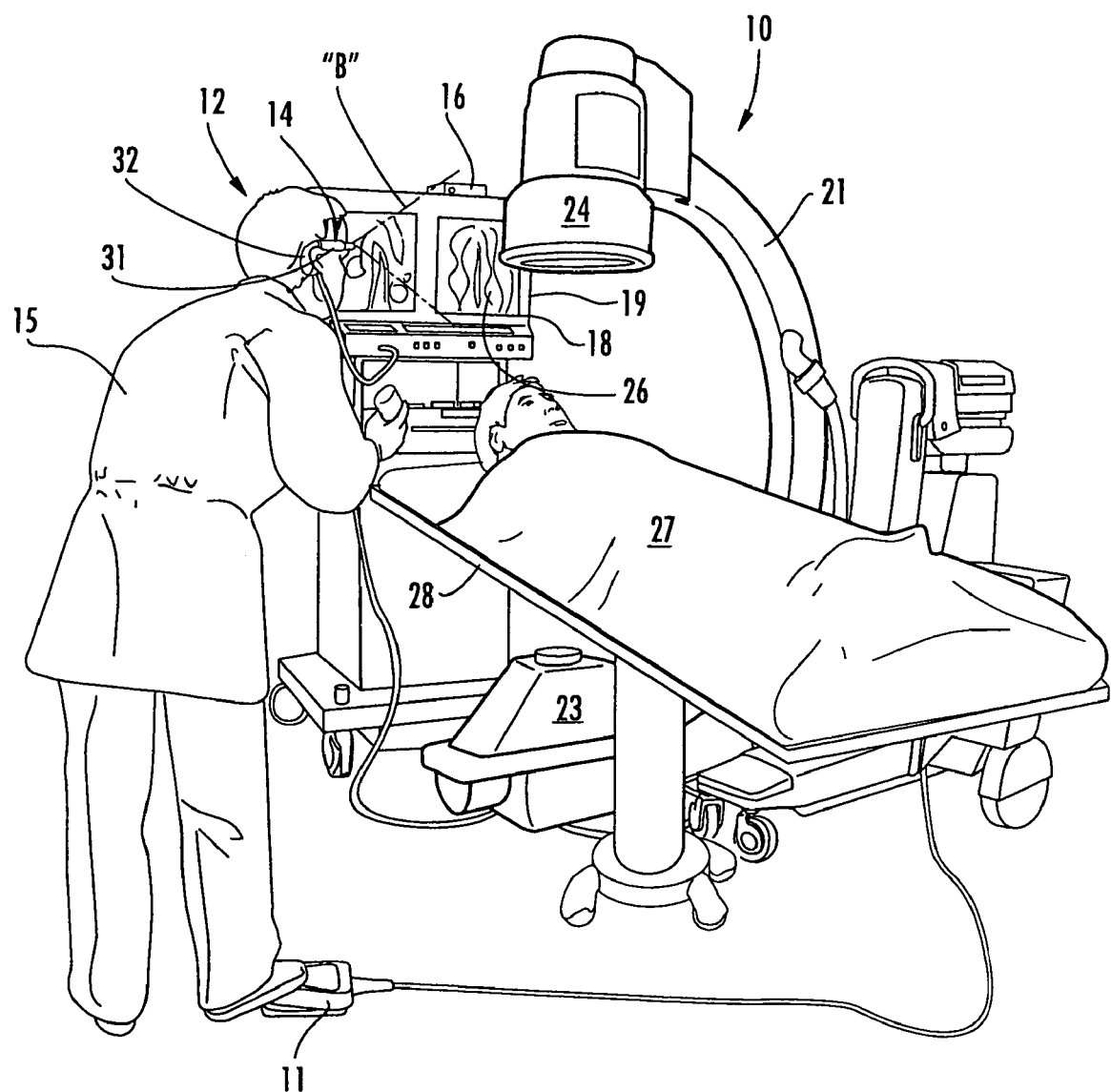
FIG. 1 is an environmental view of a fluoroscope incorporating an on-demand, multiple step control assembly according to one preferred embodiment of the present invention.

Referring now specifically to the drawings, a fluoroscope according to the present invention is illustrated in FIG. 1, and shown generally at reference numeral 10. The fluoroscope 10 incorporates an on-demand, multiple step control assembly including a fluoro foot pedal 11 and head control 12. The head control 12 comprises an infrared transmitter 14 designed for being worn by an operator 15, an infrared receiver 16 located proximate a display screen 18 of the fluoroscope monitor 19, and a battery pack (not shown) for being carried by the operator 15. Preferably, the fluoroscope 10 further comprises a C-arm 21, means for generating x-rays, an x-ray tube 23, and an image intensifier 24 coupled to a video camera 25. The image 26 captured by the video camera 25 is displayed to the operator 15 on the display screen 18 of the fluoroscope monitor 19. Alternatively, the fluoroscope 10 may incorporate a digital detector (not shown) common in more modern machines.

Upon activation of the fluoroscope 10, as described below, x-rays are generated by converting electricity from its power line into electricity that falls into the 25-150 kilo volt range. This creates a stream of electrons that are shot against a tungsten target, or anode. When the electrons hit the anode the atomic structure of the tungsten stops the electrons, causing a release of x-ray energy. This energy is focused by the x-ray tube 23 onto a body part of the patient 27 being imaged. When the beam passes through the body it hits the image intensifier 24 which increases the brightness of the image many times (e.g. ×1000 to ×5000) so that it can be viewed on the display screen 18 of the fluoroscope monitor 19. The image intensifier 24 itself is coupled to the video camera 25 that captures and encodes the two-dimensional patterns of light as a video signal from the fluoroscope 10. The signal is converted back into a pattern of light seen as the image 26 on the display screen 18.

To activate the fluoroscope 10, the operator 15 must simultaneously employ the first and second step activation means as mentioned above—i.e., the fluoro foot pedal 11 and the head control 12. The fluoro foot pedal 11 is conveniently located on the floor adjacent the examination table 28, and in an area convenient for manual actuation by the foot of the operator 15.

Figure 4:
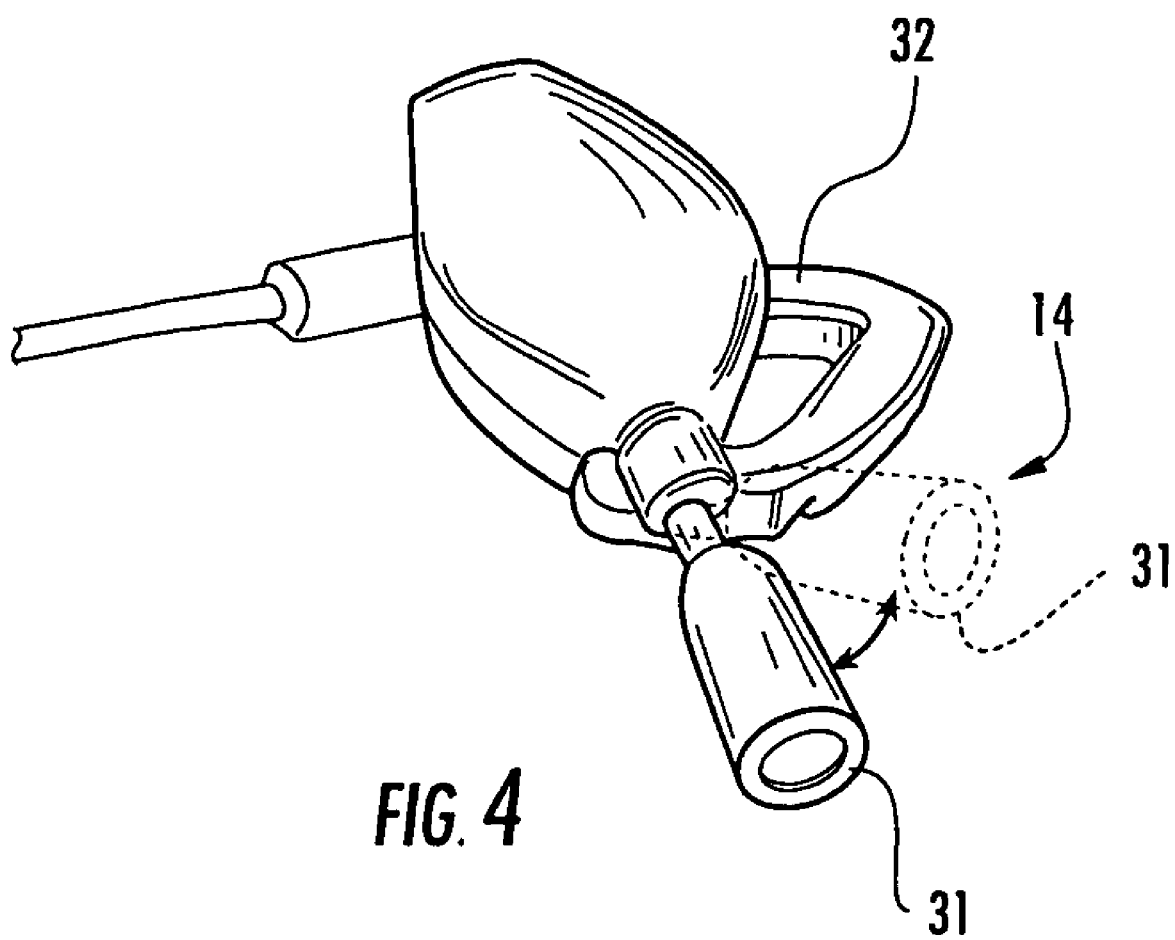
FIG. 4 is a perspective view of the ear mount and emitter cartridge, and demonstrating the adjustability of the cartridge.

The infrared transmitter 14 of the head control 12 comprises a small, lightweight emitter cartridge 31 attached to an ear mount 32 and designed for projecting a continuously-emitted, conical radiation beam "B" outwardly from the operator 15. The emitter cartridge 31 is preferably adjustable relative to the ear mount 32, as demonstrated in FIG. 4. When placed on the ear, the emitter cartridge 31 is generally aligned with the operator's line of sight such that the radiation beam "B" projects onto the display screen 18 of the fluoroscope monitor 19 when the operator 15 views the display screen 18. The infrared receiver 16 is located proximate the monitor 19, and defines a sensor zone which preferably encompasses the entire display screen 18. The sensor zone more preferably extends to a peripheral area slightly beyond the display screen 18 such that minor misalignment of the emitter cartridge 31 does not prevent intended operation of the fluoroscope 10.

Figure 2:
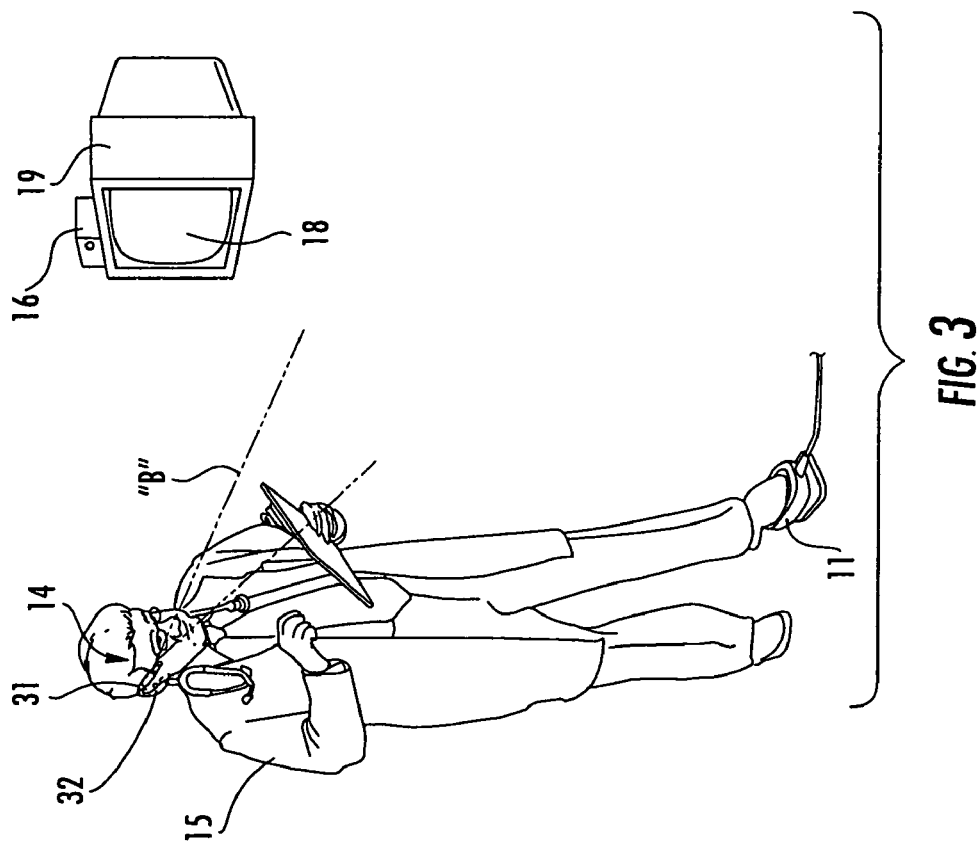
FIG. 2 is a view demonstrating simultaneous employment of the first and second step activation means for activating the fluoroscope.
Figure 3:
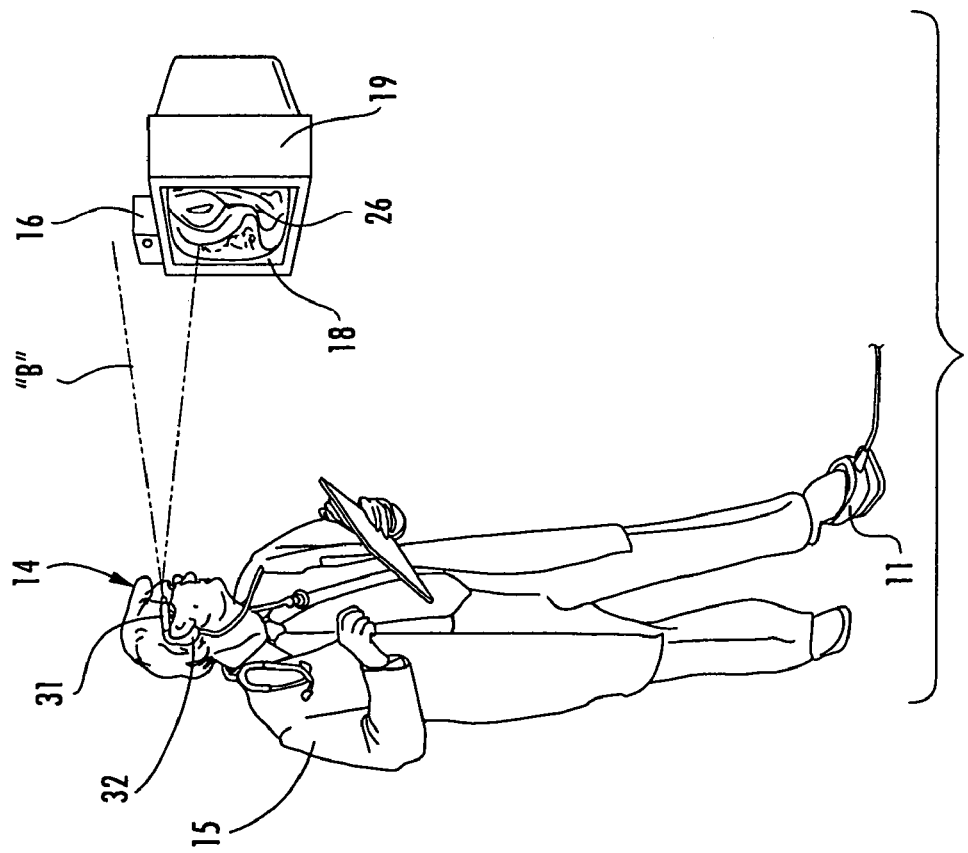
FIG. 3 is a view showing the operator's head turned away from the display screen of the fluoroscope monitor, thereby rendering the fluoroscope inoperative.

Operation of the head control 12 is generally consistent with that described in U.S. Pat. No. 5,091,926. The complete disclosure of this patent is incorporated herein by reference. When the operator 15 turns his head towards the display screen 18 of the fluoroscope monitor 19, as shown in FIG. 2, the emitter cartridge 31 projects the infrared radiation beam "B" outwardly into an area of the sensor zone. This activates a sensor, decoder, and relay of the receiver circuit. Operation of the relay disables a radiation output inhibit to the x-ray generator of the fluoroscope 10.

Figure 5:
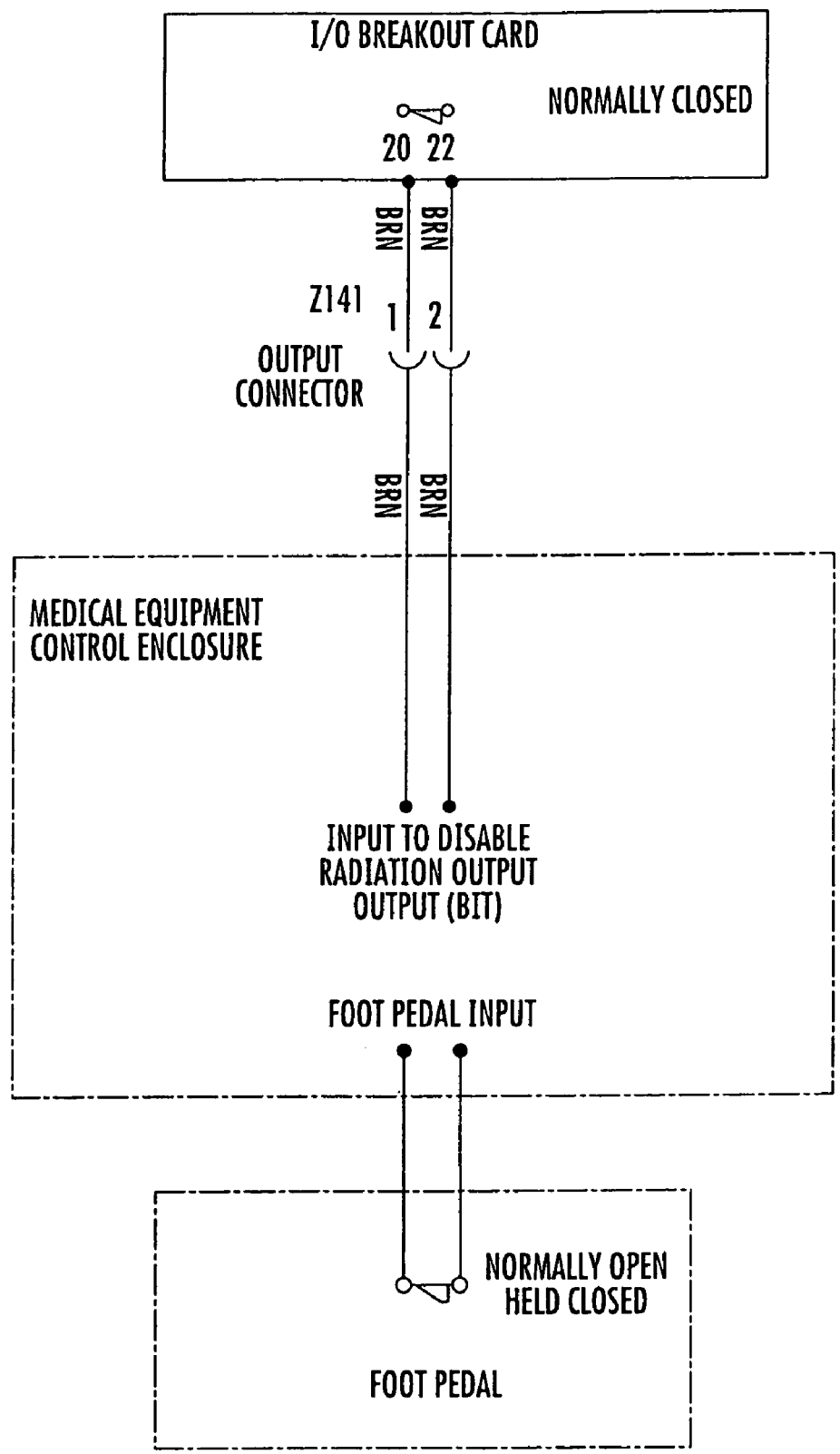
FIGS. 5 and 6 are electronic schematics illustrating the various connections of the foot and head controls.
Figure 6:
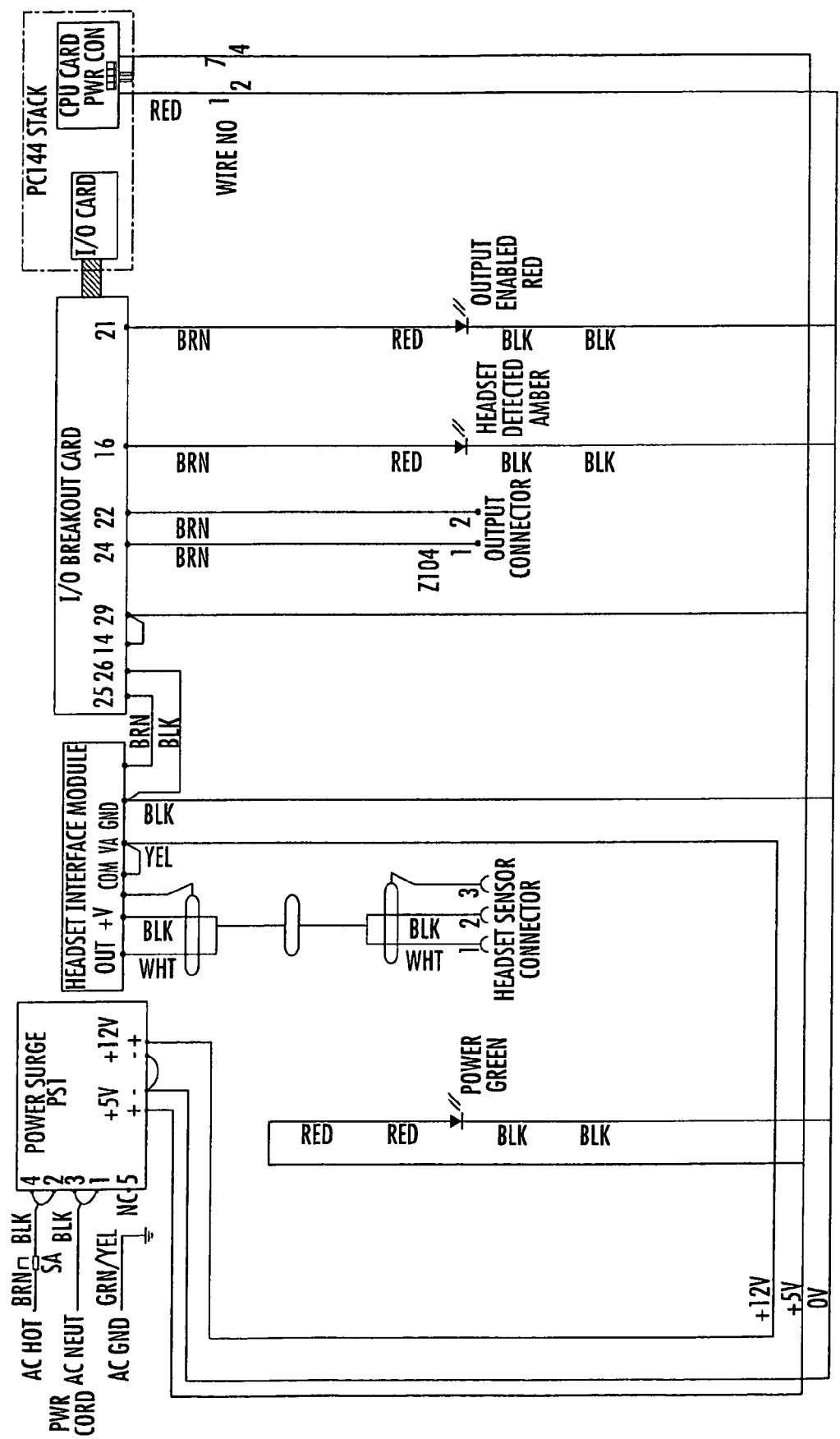

To use the fluoroscope 10, the operator 15 must first actuate the foot control by depressing the fluoro foot pedal 11. This closes an otherwise open contact 41, as indicated in FIG. 5. With the foot pedal 11 depressed, the x-ray generator is then selectively activated based on movement of the operator's head. Once the beam "B" emitted by the infrared transmitter 14 enters the sensor zone of the infrared receiver 16, the output inhibit is disabled allowing the foot control input to activate the fluoroscope 10 and irradiate the patient 27. When the operator's head turns away from the display screen 18, a normally closed contact 42 (See FIG. 5) is held open to re-enable the output inhibit and thereby render the fluoroscope 10 inoperative. The fluoroscope 10 remains inoperative (even with the foot pedal 11 depressed) until the operator's head turns back to the monitor 19 to view the display screen 18. When studying a "freeze frame", the operator 15 can simply remove his foot from the foot pedal 11 and view the display screen 18 without inadvertently activating the fluoroscope 10 and needlessly irradiating the patient 27.

An on-demand, multiple step fluoroscope control assembly is described above. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims.

I claim:

1. An on-demand multiple step fluoroscope control assembly adapted for use in a fluoroscope comprising means for generating x-rays, an x-ray tube for focusing the x-rays onto an area of a patient being imaged, and a fluoroscope monitor with a display screen for viewing the image captured by the fluoroscope, said control assembly comprising:
- a foot control adapted for being operatively connected to the fluoroscope and manually actuated by a foot of an operator, said foot control comprising a first step activation means for controlling activation of the x-ray generation means;
- a head control adapted for being operatively connected to the fluoroscope and automatically actuated when the operator views the display screen, said head control comprising a second step activation means for controlling activation of the x-ray generation means;
- whereby upon simultaneous employment of the first and second step activation means, said foot control and said head control cooperate to activate the x-ray generation means and output radiation to the patient; and in the absence of simultaneous employment of said first and second step activation means, no radiation is output to the patient.

2. A fluoroscope control assembly according to claim 1, wherein said head control comprises an infrared transmitter.

3. A fluoroscope control assembly according to claim 2, wherein said transmitter comprises an emitter cartridge for projecting an infrared radiation beam outwardly from the operator.

4. A fluoroscope control assembly according to claim 3, wherein said emitter cartridge is attached to an ear mount adapted for being worn by the operator.

5. A fluoroscope control assembly according to claim 4, wherein said emitter cartridge is pivotably adjustable relative to said ear mount to control a projection angle of said radiation beam.

6. A fluoroscope control assembly according to claim 2, and comprising an infrared receiver operatively connected to the fluoroscope and cooperating with said transmitter to actuate said head control.

7. A fluoroscope control assembly according to claim 6, wherein said receiver defines a sensor zone which encompasses the display screen of the fluoroscope monitor, such that projection of the radiation beam onto the display screen actuates said head control.

8. A method for imaging a patient using a fluoroscope comprising means for generating x-rays, said method comprising the steps of:
- actuating a foot control operatively connected to the fluoroscope;
- upon actuation of the foot control, simultaneously actuating a head control operatively connected to the fluoroscope; and
- whereby the foot control and head control cooperate to activate the x-ray generation means and output radiation to the patient, and in the absence of simultaneous actuation of the foot control and head control, no radiation is output to the patient.

* * * * *